United States Patent [19]
Adair

[11] Patent Number: 5,633,203
[45] Date of Patent: May 27, 1997

[54] METHOD OF MAKING A MINIATURIZED ELECTRONIC IMAGING CHIP FROM A STANDARD IMAGING CHIP

[76] Inventor: Edwin L. Adair, 317 Paragon Way, Castle Pines Village, Colo. 80104

[21] Appl. No.: 435,997
[22] Filed: May 5, 1995

Related U.S. Application Data

[60] Division of Ser. No. 155,996, Nov. 23, 1993, Pat. No. 5,495,114, which is a continuation-in-part of Ser. No. 954,550, Sep. 30, 1992, abandoned.

[51] Int. Cl.$^6$ .................. H01L 31/0203; H01L 31/18; H01L 21/60
[52] U.S. Cl. .................. 438/66; 438/977; 438/75
[58] Field of Search .................. 437/183, 923, 437/209, 2; 358/98

[56] References Cited

U.S. PATENT DOCUMENTS

| | | |
|---|---|---|
| 3,520,587 | 7/1970 | Tasaki et al. |
| 4,786,965 | 11/1988 | Yabe . |
| 4,862,873 | 9/1989 | Yajima et al. . |
| 4,895,431 | 1/1990 | Tsujuchi et al. . |
| 4,924,853 | 5/1990 | Jones, Jr. et al. . |
| 4,926,257 | 5/1990 | Miyazaki . |
| 5,041,396 | 8/1991 | Valero .................. 437/923 |
| 5,173,756 | 12/1992 | Wong et al. . |
| 5,318,926 | 6/1994 | Dlugokecki .................. 437/923 |

FOREIGN PATENT DOCUMENTS 57-45252  3/1982  Japan .................. 437/923

Primary Examiner—George Fourson
Assistant Examiner—Scott Kirkpatrick
Attorney, Agent, or Firm—Fields & Johnson, P.C.

[57] ABSTRACT

A miniaturized electronic imaging chip has stratified layers wherein a base silicon layer has a peripheral edge defining an area and a thickness which allows passage therethrough of most UV, visible and IR light. A pixel layer is formed on the back side of this first silicon layer. At least one interconnect layer is bonded to the pixel layer. Electric leads are bump bonded to the bonding pads on the outermost interconnect layer and extend away from it within the area for attachment to means for sensing electrical signals generated by an image projected onto the pixel layer through the silicon layer. Preferably, the leads are perpendicular to the chip. A unique method of manufacturing the miniaturized electronic imaging chip from a standard CCD comprises the steps of shaving a silicon layer, having a peripheral edge defining a second area which is smaller than the first area, on the back side of the standard CCD to a thickness which allows passage of a light image therethrough. The CCD then is reversed so that the image is projected through the shaved silicon layer. Leads are bumped bonded to the former front surface of the CCD within the smaller second area for supplying electrical signals to and from the CCD.

2 Claims, 2 Drawing Sheets

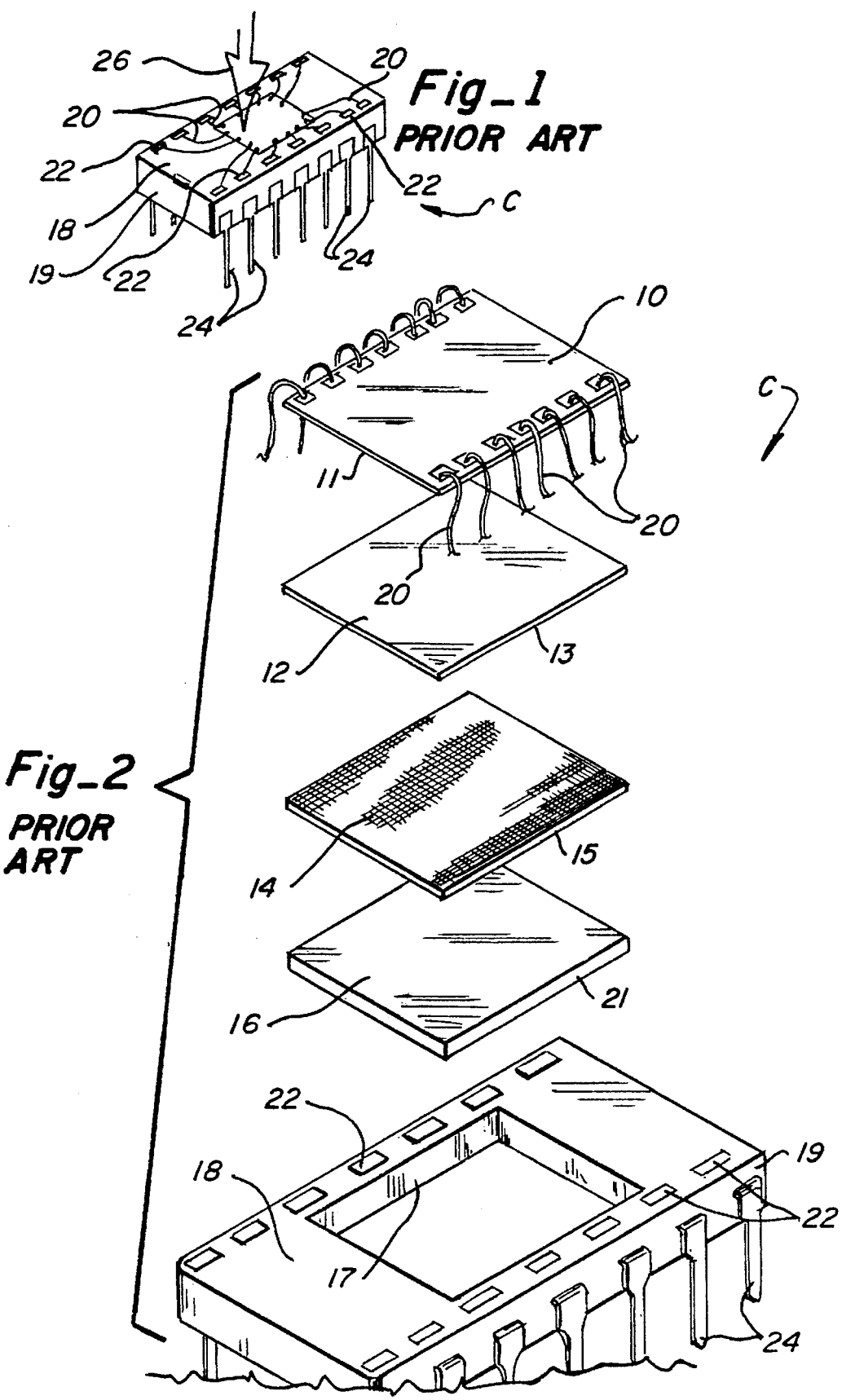

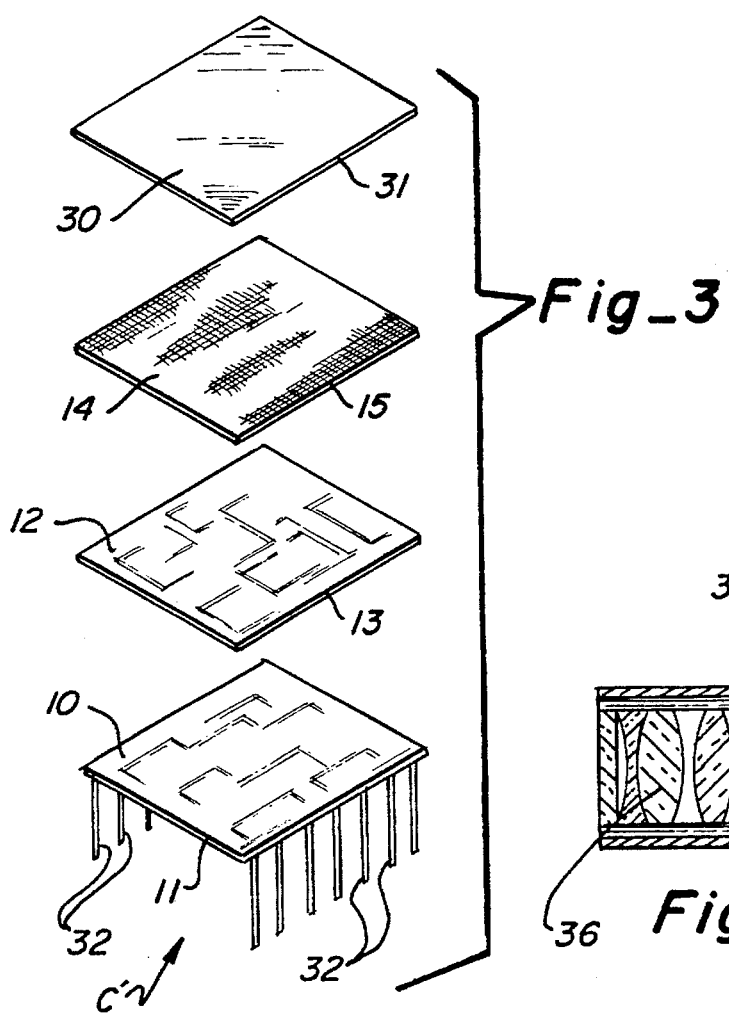
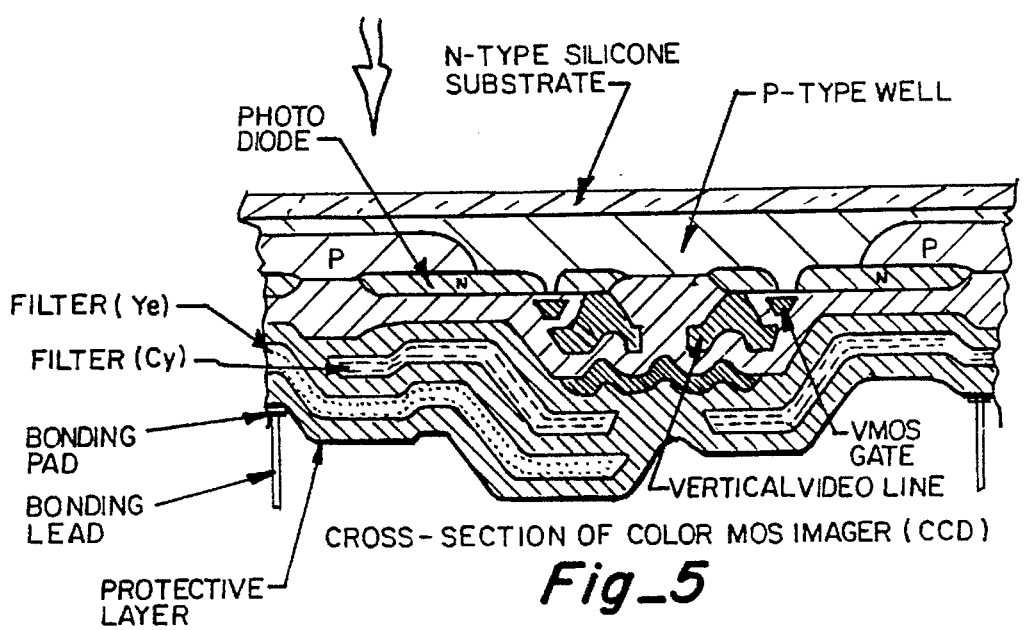

METHOD OF MAKING A MINIATURIZED ELECTRONIC IMAGING CHIP FROM A STANDARD IMAGING CHIP

This is a division of U.S. application Ser. No. 08/155,996 filed Nov. 22, 1993, now U.S. Pat. No. 5,495,114, which is a continuation in part of U.S. application Ser. No. 07/954,550 filed Sep. 30, 1992, now abandoned.

TECHNICAL FIELD

This invention relates to an electronic imaging chip and particularly to a method of modifying the architecture of a standard electronic chip to create a new miniaturized chip with enhanced capabilities.

BACKGROUND ART

Although electronic imaging chips, such as CCDs, have found extensive use in electronic imaging devices, their utilization in endoscopes has been limited because of size. The trend is to make endoscopes of ever decreasing diameter so as to be less intrusive when introduced into the body of a patient. However, the ability to reduce the diameter of the endoscope is often controlled by the size of the imaging device. The standard CCDs do not allow for miniaturization in their present configuration. Because of their relatively large size, stereoscopic imaging, especially, has not been possible in a small endoscope. In order to overcome the relatively large size of the CCD they have often been positioned longitudinally within the endoscope and used either for side viewing or in combination with a prism to provide end viewing, all of which adds to the complexity, weight, cost and ultimate size.

Examples of attempts to compensate for the large sized standard CCDs in stereoscopic endoscopes are illustrated in a number of patents.

Tasaki et al., U.S. Pat. No. 3,520,587, discloses a stereoscopic endoscope having two flexible fiber optic systems with objective lens systems being located at the distal end of each for focusing an image of the site to be inspected. An ocular is located at the proximal end of each fiber bundle for viewing the transmitted images. A visual perception in three-dimension is thereby created. This device is intended to provide a stereoscopic endoscope of limited diameter, but because of the use of light fibers for both transmitting and receiving light and the requirement for relatively sophisticated electronics, the device is still larger than desired for many applications and is quite costly.

Yabe, U.S. Pat. No. 4,786,965, discloses a conventional electronic chip structure in which a base plate is positioned behind the chip. This base plate as an extended side portion to which the leads on the chip are connected. This requires the endoscope to be of sufficient diameter to accommodate the extended side portion. Light is not transmitted through the base and it has no light transmitting qualities.

Miyazaki, U.S. Pat. No. 4,926,257, discloses a stereoscopic endoscope comprising a single solid-state image sensor and an optical image system. Stereoscopic imaging is made possible by shifting the solid-state image sensor back and forth between the two optical imaging systems. A prism system is provided in which images are sequentially transmitted to provide the three-dimensional image for viewing.

Jones, Jr. et al., U.S. Pat. No. 4,924,853, also discloses a stereoscopic endoscope using a single imaging lens whereby the image is split by a split beam prism, which images are converted to electrical signals and displayed on a television screen. The images are transmitted from the lens by means of coherent light transmitting elements. This device also provides for the alternate transmission of images to provide a three-dimensional image for viewing.

Yajima et al., U.S. Pat. No. 4,862,873, discloses a stereoscopic endoscope comprising a pair of optical guides which are capable of conducting and illuminating light to be reflected on the site to be observed. While one optical guide conducts the illuminating light, the other optical guide conducts the light from the object being observed. The optical guides can be switched from one function to the other, thereby creating a stereoscopic image.

Tsujiuchi et al., U.S. Pat. No. 4,895,431, discloses a stereoscopic endoscope in which a first endoscope image is taken at one position while a second endoscopic image is taken from a second position. The endoscopic images are partially overlapped with means for detecting the relationship between the first and second images, thereby providing a three-dimensional image.

DISCLOSURE OF THE INVENTION

In accordance with this invention a miniaturized electronic imaging chip is provided which is of the interline transfer architecture. This device comprises stratified layers wherein a base silicon layer is thin enough to allow passage therethrough of most UV, visible and IR light which strikes a pixel layer formed on the back side of the base silicon layer. Various interconnect layers including an interlace circuit, vertical shift register, horizontal shift register and an output register are terminated on the chip margins on the surface of the outermost interconnect layer as bonding site pads to allow bump bonding of electrical pins extending away from the chip for attachment to means for sensing electrical signals generated by an image projected onto the pixel layer through the base silicon layer. Preferably, the leads are bonded perpendicular to the chip surface and lie within an area defined by the peripheral edge of the silicon layer.

A unique method of manufacturing the miniaturized charged-coupled device comprises the steps of shaving a silicon layer to a sufficient thinness to allow passage of a light image therethrough. The CCD is then reversed so that the image is projected through the thin back side of the silicon substrate. Leads are bumped bonded to the former front surface of the CCD in perpendicular relation thereto so as to lie within the area defined by the peripheral edge thereof for supplying electrical signals to and from the CCD. These modifications significantly reduce the outside dimensions of the CCD architecture by totally eliminating the substrate which supports the CCD and holds the standard electrical leads and required packaging.

By this method, a CCD is provided whose surface area is no greater than that defined by the pixel layer itself. Furthermore, the total thickness of the chip is reduced. This makes the chip sufficiently small to be used in stereoscopic endoscopes and in endoscopes of very small diameter.

Additional advantages of this invention will become apparent from the description which follows, taken in conjunction with the accompanying drawings.

BRIEF DESCRIPTION OF THE DRAWINGS

FIG. 1 is a perspective view of a prior art CCD supported in an opening in a large substrate which includes the electronic packaging;

FIG. 2 is an exploded, diagrammatical, enlarged view of the CCD of FIG. 1;

FIG. 3 is an exploded, diagrammatical view of a CCD constructed in accordance with this invention;

FIG. 4 is a section showing the CCD of FIG. 3 used with a lens system in an endoscope; and FIG. 5 is a sectional view showing the architecture of a CCD constructed in accordance with this invention.

BEST MODE FOR CARRYING OUT THE INVENTION

In accordance with this invention, a method has been provided for modifying the architecture of an electronic imaging chip to substantially reduce its size and increase its capabilities. The term "imaging chip" as used herein is intended to include any of a wide range of photosensitive chips used for imaging, such as CCDs, CIDs, CPDs and MOSs. The discussion which follows will be directed specifically to a CCD chip, but it will be understood that the invention is equally applicable to the other above-mentioned chips.

FIGS. 1 and 2 show a conventional electronic chip C. The chip includes one or more interconnect layers, such as layer 10, having a peripheral edge 11, and layer 12, having a peripheral edge 13, through which an image is projected onto a pixel layer 14, having a peripheral edge 15. This layer is supported on a thick silicon base layer 16, having a peripheral edge 21 sized to just fit within and be mounted in an opening 17 in a large substrate 18, having a peripheral edge 19 which defines a first area. The substrate 18 is similar to a picture frame which provides a support for the chip and protects it from damage. This substrate may be made of any one of several materials, such as ceramic or plastic. A plurality of leads 20 connect the CCD in interconnecting layers to electrical contacts 22 on substrate 18. Electrical pins 24 are connected to the substrate and to electrical contacts 22, along the margins, as shown, for connection to electrical wires (not shown) for transmitting electrical information into and out of the chip. It will be noted that the images projected in the direction of arrow 26 shown in FIG. 1, must be projected through interconnect layers 10 and 12 onto pixel layer 14 thereby reducing the amount of light that can be transmitted to the pixel layer. The light which does pass through the interconnect layers is distorted by them, resulting in a distorted image being projected onto the pixel layer. Also, since substrate 18 is substantially bigger in area than pixel layer 14, a significantly larger area is required by the chip than the area occupied by the pixel layer and the associated layers above and below it.

By the method of the present invention, an improved chip of the type shown in FIGS. 3 and 4 is provided. In this regard, the chip C is removed from substrate 18 and turned over so that silicon layer 16 is at the top. Next, silicon layer 16 is shaved down to a sufficiently thin thickness to allow the transmission of a light image. The desired thickness will vary depending on the particular application. An acceptable thickness range has been found to be between 3 and 200 microns. A preferred range is between 6 and 10 microns. After shaving, a thin layer 30 is formed, having a peripheral edge 31 defining a second area, which is smaller than the first area defined by peripheral edge 19. After reversing the chip, interconnect layers 10 and 12 are mounted below pixel layer 14, as shown, and posts 32 are indium bump bonded to interconnect layer 10 and extend generally perpendicular thereto within the second area to provide electrical connections for bringing data into and out of the chip. Advantageously, the posts are positioned within the area defined by peripheral edge 15 of pixel layer 14. With this arrangement, the area of modified chip C' is no larger than the area of pixel layer 14, such as 2 mm square.

This allows the modified chip C' to be placed inside an endoscope 34 having a diameter no larger than 3 or 4 mm. The chip is shown near the distal end of endoscope 34, as shown in FIG. 4, with an appropriate lens system 36 for focusing an image on the chip. Because of the thinness of silicon layer 30 and the fact that the light does not need to pass through the interconnect layers 10 and 12, it is possible for pixel layer 14 to receive up to 90% of UV or infrared light in addition to light in the visible light range. Thus, the use of the chip is enhanced for a wider light spectrum thereby increasing its utility. In some applications, filters can be placed over the chip to regulate the frequency of light being utilized by the CCD. In addition, since the light does not have to pass through the interconnect layers, there is less distortion of the image as it is projected onto the pixel layer. Also, a chip constructed in the manner of chip C' can be autoclaved whereas the conventional chip and packaging will be damaged or destroyed by the high temperatures required for autoclaving. Because of the miniaturization of chip C', a pair of such chips can be used in side-by-side relationship within a stereoscopic endoscope without resulting in an endoscope of excessively large diameter. Also, they can be used alone to provide a very miniaturized endoscope, as discussed above, for use in passageways and through trochars in a less intrusive manner than that which was previously possible.

In the foregoing description the pixel layer and interconnect layers have been described as being separate distinct layers. In reality, the elements that make up the chip are stratified, as shown in FIG. 5 and as is well understood by those skilled in the art of the construction of CCDs. Therefore, the term "layers" as used herein is intended to cover the pixel layer and interconnect layers in the more integrated and stratified arrangement shown in FIG. 5.

This invention has been described in detail with reference to a particular embodiment thereof, but it will be understood that various other modifications can be effected within the spirit and scope of this invention.

I claim:

1. A method of forming a miniaturized electronic imaging chip from a standard imaging chip, the standard imaging chip having a substrate with a first peripheral edge defining a first area, and having stratified layers which include at least one interconnect layer, through which an image is normally projected, a pixel layer for receiving the image, a silicon layer having a second peripheral edge defining a second area which is smaller than the first area, the substrate being connected to first ends of connector pins, and having electrical leads connected between the interconnect layer and electrical contacts on the substrate to which the first ends of the connector pins are attached, the connector pins having second ends attached to circuitry which incorporates the standard imaging chip, said method comprising the steps of:

removing the electrical leads;

removing the at least one interconnect layer, pixel layer, and silicon layer from the substrate;

shaving the silicon layer to a thickness which allows passage of a light image therethrough;

bump bonding new lead to the interconnect layer within the second area of the shaved silicon layer; and reversing the chip so that a light image is projectable through the shaved silicon layer, the new leads being directly attachable to the circuitry.

2. A method, as claimed in claim 1, including the further step of:

projecting an image onto the pixel layer through the shaved silicon layer.

* * * * *

UNITED STATES PATENT AND TRADEMARK OFFICE
CERTIFICATE OF CORRECTION

PATENT NO. : 5,633,203
DATED : May 27, 1997
INVENTOR(S) : Edwin L. Adair

It is certified that error appears in the above-indentified patent and that said Letters Patent is hereby corrected as shown below:

Title page, [60], delete "Nov. 23, 1993" and insert --Nov. 22, 1993--;
   Column 2, lines 38 and 39, delete "thin back side of silicon substrate" and insert --shaved silicon layer--;
   Column 4, line 54, delete "lead" and insert --leads--.

Signed and Sealed this

Twelfth Day of January, 1999

Attest:

Attesting Officer     *Acting Commissioner of Patents and Trademarks*